United States Patent [19]

Okochi et al.

[11] 4,200,434

[45] Apr. 29, 1980

[54] IMMUNOLOGICAL BLOOD TEST METHOD

[75] Inventors: Kazuo Okochi; Hiroyuki Kiyokawa, both of Fukuoka, Japan

[73] Assignee: Sanki Engineering Ltd., Nagaokakyo, Japan

[21] Appl. No.: 881,051

[22] Filed: Feb. 24, 1978

[30] Foreign Application Priority Data

Feb. 24, 1977 [JP] Japan ................... 52/19614

[51] Int. Cl.$^2$ ........................................... G01N 33/16
[52] U.S. Cl. ........................... 23/230 B; 233/25; 422/72; 424/11; 424/12
[58] Field of Search .............. 23/230 B, 253 R; 128/2G; 233/25; 424/11, 12

[56] References Cited

U.S. PATENT DOCUMENTS

| | | | |
|---|---|---|---|
| 3,734,079 | 5/1973 | Weber | 23/253 R X |
| 3,775,309 | 11/1973 | Ito | 233/25 |
| 3,848,796 | 11/1974 | Bull | 233/25 |
| 3,885,735 | 5/1975 | Westberg | 233/25 |
| 3,910,103 | 10/1975 | Rose | 23/230 B X |
| 3,982,895 | 9/1976 | Amos | 23/230 B |
| 4,045,175 | 8/1977 | Weber | 23/230 B |
| 4,058,460 | 11/1977 | Ito | 233/25 X |
| 4,062,936 | 12/1977 | Ogawa | 23/230 B X |

OTHER PUBLICATIONS

"Clinical Diagnosis", I. Davidson et al., eds., 14th Edition, 149-155, W. B. Saunders Co., Phila., 1969.
K. Takagi et al., Journal of Clinical Blood, 17(11), 1153-1160 (1976).
K. Kitazima et al., Journal of Laboratory and Clinical Medicine, 85, 855-864 (1975).
S. Ogita et al., Journal of Japanese Society of Obstetrics and Gynecology, 27(10), 1099-1102 (1975).

*Primary Examiner*—Sidney Marantz
*Attorney, Agent, or Firm*—Wenderoth, Lind & Ponack

[57] ABSTRACT

A method for immunological blood testing carried out by the use of a coil column, composed of a transparent tube helically wound on a support rod. To carry out the test, the coil column filled with a liquid solution of a polymer compound is, after a droplet of blood to be tested has been introduced into the liquid solution within the tube, centrifuged while undergoing a planetary motion to allow erythrocytes to sediment.

5 Claims, No Drawings

IMMUNOLOGICAL BLOOD TEST METHOD

BACKGROUND OF THE INVENTION

The present invention relates to an immunological blood test method and a coil column for use in such method.

More particularly, the present invention relates to an immunological blood test method and a coil column adapted to be used in the practice of the immunological blood test according to a known coil planet centrifuge (CPC) method. The present invention adopts such method to use in measuring erythrocyte sedimentation rate.

According to a conventional immunological blood test method, a reaction in serum is caused to take place on a glass place and a diagnosis is made on the basis of microscopic examination of coagulation of erythrocytes. However, improvements in this method have been desired, since it demands a considerable number of complicated and time-consuming procedures to be performed by an analyst. Moreover, it takes a relatively long period of time to complete the analysis, since coagulation of erythrocytes must be sufficient to permit the microscopic examination.

According to the CPC method, a small amount of blood is introduced into one end of an elongated tube which is helically wound around a support rod and contains a saline solution having a linear concentration gradient. This coil column, composed of the tube and the support rod with the saline solution filled in said tube, is caused to simultaneously revolve and undergo a planetary motion so that there can be produced a hematological pattern, which permits diagnosis of blood, liver, bile or gastrointestinal disorders or potential hemolytic disorders in infants. (See, K. Takagi et al.: "Journal of Clinical Blood", Vol. 17, No. 11, Pages 1153 to 1160 (1976); Kitazima, et al.: "Journal of Laboratory and Clinical Medicine", Vol. 85, page 855 to 864 (1975); and S. Ogita et at.: "Journal of Japanese Society of Obstetrics and Gynecology", Vol. 27, No. 10, pages 1099–1102 (1975).)

However, no attempts have been made to apply the CPC method to immunological blood tests.

SUMMARY OF THE INVENTION

In consideration of these facts, the inventors of the present invention conducted a study whose results showed the immunological blood tests can be effected by observing sedimentation rates of erythrocytes in particular liquid solutions and that elongated tubes containing these solutions are optimally suited to carrying out the blood tests, these research results leading to the present invention.

The main features of the present invention are an immunological blood test method according to which sedimentation of erythrocytes in a liquid solution of a polymer compound is effected and rate of sedimentation of measured whereby antibody-sensitized corpuscles are detected, and an erythrocyte sedimentation rate measuring coil column composed of a plurality of turns of a helically wound transparent tube containing a liquid solution of a polymer compound.

DETAILED DESCRIPTION OF THE INVENTION

Polymer compounds which are suitable for use in the method of the invention include natural or synthetic polymer compounds capable of forming viscous aqueous solutions, for example, natural polymer compounds such as albumin and dextran, and synthetic polymer compounds such as ficoll, polyethylene glycol and polyvinylpyrollidone .

The concentration of the natural or synthetic polymer compound solution employed is adjusted with reference to the viscosity and the specific gravity of the polymer compound containing solution. The range of viscosity of the solution is 1.1 to 50.0 c.p.s. and, preferably, 1.15 to 12.0 c.p.s. and the range of specific gravity is 1.01 to 1.23 and, preferably, 1.01 to 1.15. [The requisite proportion of polymer compound in the solution varies depending on the type of the polymer compound employed, but is of the order of 0.1 to 10% by weight for most general purposes and, preferably, of the order of 0.2 to 2% by weight.] If the viscosity, the specific gravity or the concentration of the polymer compound containing solution is too high, this is undesirable since the resistance to sedimentation of erythrocytes becomes great and the rate of sedimentation becomes slow. On the other hand, it is also undesirable if the viscosity, the specific density or the concentration is too low, since in this case it becomes difficult to distinguish between the rate of sedimentation of normocytes and that of antibody-sensitized corpuscles.

According to the method of the present invention, erythrocytes are added to the polymer compound containing solution and the difference in rate of sedimentation of the erythrocytes in the solution is measured. The amount of the erythrocytes may be small, about $5\mu$ liter being normally sufficient.

After the addition of erythrocytes to the solution, a centrifugation is effected to allow the erythrocytes to sediment to measure the rate of sedimentation, a satisfactory sedimentation being achieved in about 10 minutes if the centrifugation is such as to cause application of a centrifugal force of, for example, 300 G. During the sedimentation under the influence of the centrifugal force, since the erythrocytes sediments in the direction in which the centrifugal force acts, the apparent up-side may be moved upwards.

During the above described sedimentation under the influence of the centrifugal force, the temperature is preferably maintained constant at a value not exceeding 50° C.

Prior to the sedimentation, the erythrocytes are brought into contact with antigens corresponding to the antibodies which are the object of the test, this contact resulting in coagulation only of antibody-sensitized corpuscles. This process may be effected by the same procedure as is normally employed for the conventional direct Coombs test or the indirect Coombs test. However, in the method according to the present invention, it is not necessary that there be coagulation of a sufficient number of erythrocytes to permit microscopic detection, but detection is satisfactorily achieved when there is coagulation of only a few to a few tens of erythrocytes.

According to the method of the present invention, the polymer compound containing solution employed may contain an inactive substance, such as sodium chloride, for example, which has no effect on coagulation of blood.

According to the method of the present invention it is preferable that the osmotic pressure of the polymer compound containing solution be generally equal to that of erythrocytes. A large difference between the osmotic pressure of these elements is undesirable since it is liable to result in hemolysis, or otherwise, release of water, by erythrocytes.

In observation of the rate of sedimentation of the erythrocytes thus added to a natural or synthetic polymer compound containing solution, it is seen that antibody-sensitized erythrocytes coagulate and sediment more rapidly than normocytes. Thus, it is possible to determine whether or not erythrocytes are affected by antibodies and to determine the extent to which the erythrocytes are affected by antibodies.

To practise the method of the present invention, there is suitably made use of a coil column such as employed for the corpuscle analysis system conventionally known as the CPC system, which is filled with a natural or synthetic polymer compound containing solution.

As a measuring coil column according to the present invention, there is employed a coil column which is composed of a plurality of turns of a helically wound transparent tube which, for most general purposes, has an inner diameter within the range of 0.3 to 1.5 mm. and a length of 3 m. However, it is sufficient if the inner diameter of the transparent tube is large enough to permit free movement of the various cell groups in the blood, and the length of the tube is not critical. The tube must be transparent in order to permit the solvent and cell groups therein to be seen without difficulty from the exterior and from the point of view of facility of forming the tube into a coil, the tube should be flexible to permit winding the transparent tube around a support rod which is also preferably transparent and which has a diameter within the range of 5 to 20 mm., the transparent tube being wound helically around the support rod. There are no special requirements concerning the direction of winding of the transparent tube on the support rod or the pitch or number of turns, but even winding of the tube is preferable.

The coil column according to the present invention, which is constructed as hereinbefore described, is filled with the above mentioned polymer compound containing solution. Unlike the means employed in the CPC method, in which there is produced a linear concentration gradient of the contained salt solution, the coil column of the present invention does not require any particular concentration gradient.

In employment of the coil column according to the present invention, a small amount of erythrocytes is introduced into one end of the tube and then as in the CPC method, both ends of the tube are sealed and centrifugation-sedimentation is effected in a centrifuge which rotates and revolves the coil column, thus making it possible to easily detect antibody-sensitized erythrocytes. It is sufficient if the speed of rotation of the coil column about its own axis is within the range of 1 to 2 r.p.m. and the radius and speed of revolution thereof are respectively within the range of 20 to 25 cm. and 1,000 to 2,000 r.p.m. The period during which the coil column is centrifuged while undergoing the planetary motion is simply made such as to achieve the required degree of sedimentation.

As opposed to the sedimentation rate proportional to the square of the radius of a cluster of coagulated erythrocytes which is achieved when an ordinary centrifuge is employed, when a blood test is effected using the coil column of the invention and effecting centrifugation sedimentation by means of a centrifuge which causes rotation and revolution of the coil column, the sedimentation rate is proportional to the fourth power of the radius of coagulation clusters, and it is therefore very easy to detect antibody-sensitized erythrocytes.

The present invention makes it possible to detect antibody-sensitized erythrocytes quantitatively and more precisely than in the conventional direct Coomb's test and indirect Coomb's test, and also makes detection possible even if erythrocytes are only weakly sensitive to antibodies and only a few erythrocytes coagulate.

The invention will be described in greater detail hereinafter in reference to specific examples thereof. The scope of the present invention is of cource not limited in any way to the specific examples described, but may extend to the scope of the above described main features.

EXAMPLE I

Erythrocytes sensitized due to incompleteness of antibodies and samples of antibody-sensitized and autoantibody-sensitized erythrocytes of the same blood type, as indicated in Table 1, were placed in coil columns and, without the sample material being cleansed with a physiological salt solution, the material was centrifuged by being rotated 3,000 times in a period of 3 minutes, whereby a sedimentation deposit was obtained.

Each coil column was constituted by 150 turns of a tightly wound polyethylene tube having an inner diameter of 0.3 mm. and a length of 3 m. and filled with a 17 to 22% aqueous solution of albumin, to which was added 5μ liter of the above mentioned sedimentation deposit. Centrifugation was effected by causing rotation of the coil columns at a speed of 16 r.p.m. and revolution thereof at a speed of 1,600 r.p.m., radius of revolution being 22.5 cm, for 10 minutes, at a temperature of 37° C. Thereafter, a microscopic examination of the coil columns was made to determine the positions of erythrocytes. Results of the various tests are shown in Table 1 which, for the purpose of comparison, also shows results when normocytes are employed.

Table I

| | Age | Type of Antibody | Travel of Erythrocytes (No. of coil turns) | Remarks |
| --- | --- | --- | --- | --- |
| Invention 1 | Foetus (Blood of umbilical cord) | anti-D | 42 | A portion of the sedimented erythrocytes went completely to the other end of the 3m tube of the coil column. |
| 2 | Infant (14 days old) | anti-Di$^b$ | 14 | |
| 3 | Infant (14 days | | | |

Table I-continued

| | | Age | Type of Antibody | Travel of Erythrocytes (No. of coil turns) | Remarks |
|---|---|---|---|---|---|
| | | old) | anti-Di$^b$ | 17 | |
| | 4 | Adult (49 years old) | auto-antibody | 15 | |
| | 5 | Adult (45 years old) | auto-antibody | 32 | A portion of the sedimented erythrocytes went completely to the other end of the 3m tube of the coil column. |
| Comp | 1 | Adult | — | 9–10 | |
| | 2 | Foetus (Blood of umbilical cord) | — | 9–10 | |

COMPARISON

The same type of corpuscles as used in Nos. 1 to 5 under Example I were employed and measurements were made by the procedures of the indirect Coomb's test method and the direct Coomb's test method, results obtained being shown in Table II.

Table II

| Nos. in Table I | Indirect Coomb's Method | Direct Coomb's Method |
|---|---|---|
| 1 | 128* | +++ |
| 2 | 64* | ± |
| 3 | 64* | + |
| 4 | 2 | + |
| 5 | 16 | +++ |

Note
*dependent on antibodies of the mother.

From these results, it is seen that, in comparison with travel of normocytes, for erythrocytes sensitized by incomplete D antibodies in the coil columns, there is a tendency for travel to be faster as the amount of antibodies employed for sensitization is greater. The same tendency was observed in examples of umbilical cord blood sensitized by Rh required exchange transfusion of blood.

Results obtained by the method of the invention and those obtained by the direct Coomb's test are closely comparable.

EXAMPLE II

Procedure was the same as for Example I described above except that polyvinylpyrollidone was employed instead of albumin, and results obtained matched well with the other results.

What is claimed is:

1. An immunoassay for detecting a particular antibody in a blood sample, said antibody being associated with the erythrocytes in the blood as antibody-sensitized erythrocytes comprising:
   (a) contacting the erythrocytes with an antigen immunologically corresponding to said antibody,
   (b) introducing the antigen-contacted erythrocytes into a liquid solution of a polymer compound, said liquid solution being contained in a coil comprising a transparent tube helically wound on a support rod,
   (c) subjecting the contents of the coil to a centrifugal field produced by simultaneously rotating and revolving the coil,
   (d) measuring the erythrocytes sedimentation rate; and
   (e) correlating the rate of erythrocyte sedimentation to any presence of said particular antibody.

2. A method as claimed in claim 1, wherein said polymer compound is a protein.

3. A method as claimed in claim 2, wherein said protein is serum albumin.

4. A method as claimed in claim 1, wherein said polymer compound is polyvinylpyrollidone.

5. A method as claimed in claim 1, wherein said sedimentation is effected under the effect of a centrifugal force.

* * * * *